United States Patent
Webb et al.

[11] Patent Number: 5,974,708
[45] Date of Patent: *Nov. 2, 1999

[54] INTRAVENOUS LINE IDENTIFICATION SYSTEM

[75] Inventors: Nicholas J. Webb, Wrightwood, Calif.; David S. Jacobson, Hartsdale, N.Y.

[73] Assignee: Trauma Technologies, LLC, Memphis, Tenn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/916,688

[22] Filed: Aug. 22, 1997

[51] Int. Cl.$^6$ .................................................. G09F 3/00
[52] U.S. Cl. .............................................. 40/316; 40/666
[58] Field of Search ............................... 40/316, 317, 322, 40/331, 334, 658, 666, 628, 660, 665; 24/339, 563, 3.4, 597, 115 F, 543, 704.1

[56] References Cited

U.S. PATENT DOCUMENTS

| | | | |
|---|---|---|---|
| 3,698,383 | 10/1972 | Baucom | 128/2 G |
| 4,150,673 | 4/1979 | Watt | 128/272 |
| 4,198,773 | 4/1980 | Batts et al. | 40/322 |
| 4,256,132 | 3/1981 | Gunter | 137/14 |
| 4,308,642 | 1/1982 | Heyman | 24/306 |
| 4,654,026 | 3/1987 | Underwood | 604/80 |
| 4,775,121 | 10/1988 | Carty | 24/543 X |
| 4,795,429 | 1/1989 | Feldstein | 604/80 |
| 4,884,827 | 12/1989 | Kelley | 40/316 X |
| 4,947,568 | 8/1990 | DeBarbieri | 40/316 |
| 4,988,338 | 1/1991 | Taylor et al. | 604/180 |
| 5,157,853 | 10/1992 | Piana et al. | 40/316 |
| 5,224,674 | 7/1993 | Simons | 248/68.1 |
| 5,224,932 | 7/1993 | Lappas | 604/80 |
| 5,316,246 | 5/1994 | Scott et al. | 248/68.1 |
| 5,336,179 | 8/1994 | Ryan | 604/80 |
| 5,389,082 | 2/1995 | Baugues et al. | 24/543 X |
| 5,423,750 | 6/1995 | Spiller | 604/80 |

FOREIGN PATENT DOCUMENTS 1039122  8/1966  United Kingdom ............... 40/316

*Primary Examiner*—Brian K. Green
*Attorney, Agent, or Firm*—David P. Gordon; David S. Jacobson; Thomas A. Gallagher

[57] ABSTRACT

An intravenous line identification system includes a plurality of sets of at least two identifying tags, each set used for identifying a medicinal source and a medicinal output for one of a plurality of intravenous lines. Each set is provided with a highly visible color distinct from every other set. Each tag in a set is coupled to another tag in the same set by at least one frangible or decouplable connection. Each tag further has an opening enabling the tag to be inserted over the intravenous line, and a preferably circular hole, about which the tag holds the intravenous line. For each intravenous line, the tags are applied over the intravenous line as a set, i.e., while coupled. Once on the intravenous line the tags are decoupled from each other and slid in opposite directions along the line toward the medicinal source and output. A number of benefits are provided by the system. First, due to the high visibility of the tags, quick identification by a health care worker of a medicinal source to an output is possible. Second, because the tags are provided to the intravenous line while coupled together, any risk of misidentification of a line is eliminated. Third, setup of the identifying tags on an intravenous line is rapid, as the tags may be quickly placed over the line and separated. Fourth, the tags may be used with currently existing intravenous lines.

24 Claims, 7 Drawing Sheets

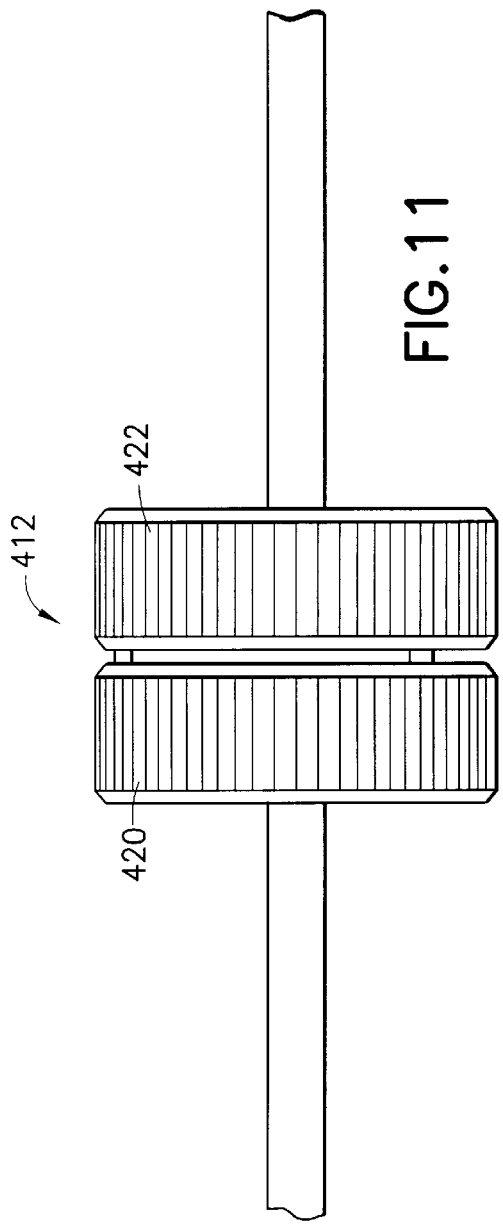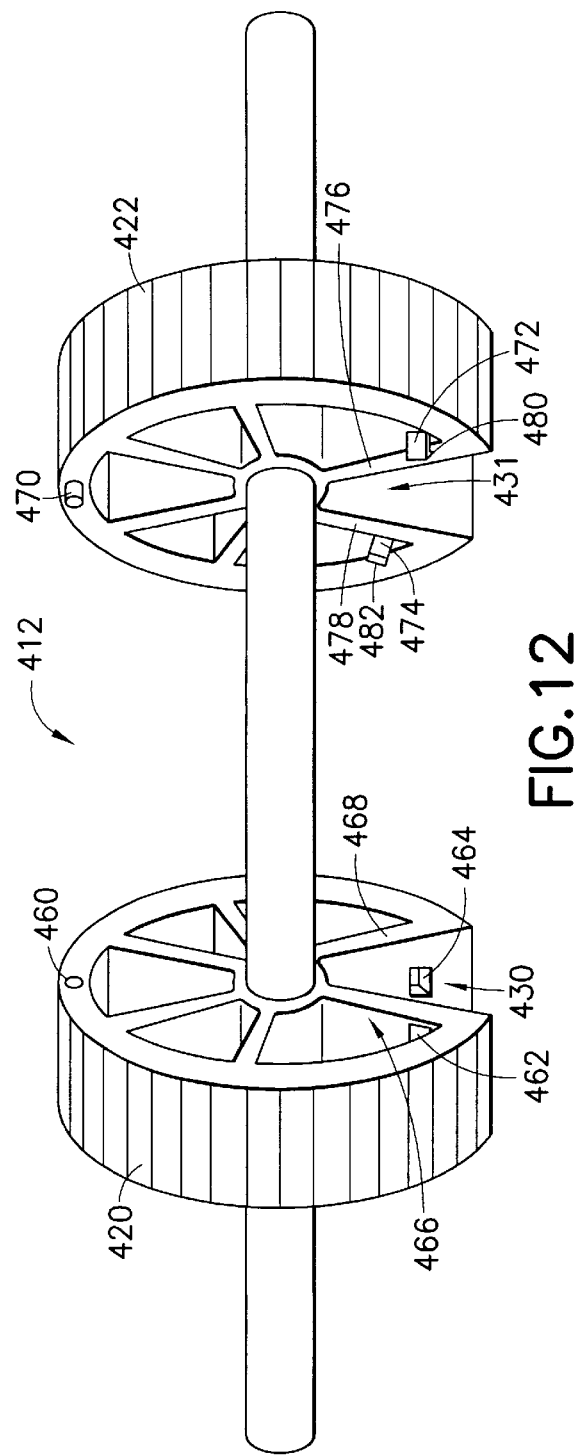

INTRAVENOUS LINE IDENTIFICATION SYSTEM

BACKGROUND OF THE INVENTION

1. Field of the Invention

This invention relates broadly to systems for the intravenous administration of medicaments and/or nutrients. More particularly, this invention relates to systems for distinctly identifying each of several intravenous lines used to intravenously administer medicaments and/or nutrients.

2. State of the Art

In a hospital setting patients are often administered liquid medicaments and nutrients (hereinafter collectively referred to as medicaments) via intravenous lines. Intravenous lines generally consist of flexible, plastic tubing connected at one end to an intravenous fluid source and at another end to a vasopuncture device which is inserted into a blood vessel of the patient. It is not uncommon for a plurality of intravenous lines, each connected to a different source of intravenous fluid, to be used simultaneously to deliver several medicaments at once to a single patient. It is also not uncommon for the vasopuncture devices to be located adjacent one another, e.g., in the brachial vein running through the arm.

As a result, the simultaneous use of multiple intravenous fluid lines can create a problem with the quick identification of a particular medicament source with a particular medicament output. This problem is aggravated by the tendency of each of the intravenous lines to coil (back to their packaged configuration) and consequently tangle with other lines.

Quick identification of a medicinal fluid source is often required in emergency situations. For example, when a patient hooked up to multiple intravenous lines is in need of emergency intravenous administration of a medication not currently being provided through the intravenous lines, it is necessary to immediately provide that medication. If a blood vessel cannot rapidly be located into which to inject the medication (often a problem because the most accessible vessels are already occupied with vasopuncture devices), it is common practice to provide the drug into a line in which a medication is already being administered; i.e., to "piggyback" an additional intravenous line with the exiting line. However, the person administering the drug must be sure that the line onto which the additional line is "piggybacked" is carrying a medicament which is "compatible" with the piggybacked medicament. Severe results may occur when a drug is inadvertently injected into a line in which the medicament flowing therethrough is not compatible with the injected or "piggybacked" medicament. For example, if heparin is inadvertently injected into a line through which lidocaine is already flowing, a flakey precipitate will form in the mixture which can be dangerous to a patient.

Yet, it is not an easy matter to distinguish one line from another line in the time constraints created by a medical emergency. As a result, a number of devices have been proposed to provide to health care workers systems for more rapidly identifying a medicament flowing through an intravenous line. For example, U.S. Pat. No. 5,224,674 to Simons discloses a tray having a plurality of retaining clips for linearly organizing intravenous lines, and a lid which covers the tray. Portions of the lines are placed in parallel orientation into the tray and the lid is placed over the tray. The lid is provided with spaces for labeling which medicaments flow through the lines respectively clipped beneath the labels on the lid. While providing some degree of organization to the lines, the device fails to meet current health care needs for several reasons. First, the time for setting up the device is generally not available under the cost constraints posed by managed health care. Managed health care attempts to mitigate costs; however, the device requires a relatively large amount of health care worker time to organize the lines within the tray and to label the cover with the various medicaments. Second, as health care workers are unlikely to label the tray lid until after all the lines have been inserted into the tray and the lid is placed over the lines, a potential for error is created. Lines, already tangled, may be misidentified, thereby defeating a dominant purpose of the device. Misidentifications can lead directly to patient health risk. The device, therefore, fails to alleviate another concern of managed health care, the reduction of catastrophic liability. Third, even if the health care worker properly identifies the lines, the health care worker is not able to rapidly identify the source and output of a particular line, as the worker must walk over to the tray, read a medicament label on the lid, and follow the line beneath the lid associated with the medicament label to its output. Such a procedure is inadequate for an emergency situation, where identification of a source with an output is required in a "time is of the essence" situation.

Another potential solution has been to provide a distinct appearing intravenous line between each source and its output. For example, U.S. Pat. No. 4,654,026 to Underwood discloses a plurality of transparent intravenous lines, each having distinct indicia disposed at intervals over its length and thereby providing an identification of a source with an output. U.S. Pat. No. 5,224,932 to Lappas discloses a combination of distinctly translucently colored intravenous lines and medicament reservoirs in which a line is paired with a reservoir having the same color, thereby providing a visual indication of source with output. U.S. Pat. No. 5,423, 750 to Spiller discloses intravenous lines which are differently transparently colored and have a portion adjacent the output which is clear. Colored indicia matching the color of a respective line is applied to the medicament reservoir coupled to that line. While each of the above intravenous line systems provides source to output indications, there are drawbacks. First, any hospital desiring to use one of the above systems will also want to continue to use standard intravenous lines where possible (e.g., where only a single intravenous line is connected to a patient) due to the reduced cost of standard intravenous lines, and the relative expense of breaking up a set of colored lines or indicia-provided lines in order to use only a single line. Keeping the above systems and standard intravenous lines together in a hospital is both expensive and space consuming. The expense, in particular, is a concern in managed health care systems. Moreover, while providing source to output indications, the indicia and colors of the above systems when provided to translucent or transparent lines are difficult to see in low light situations. Brighter colors or more distinct indicia could only be provided with opaque lines. However, it is necessary for health care workers to be able to see the fluid activity within the lines, and as a result, opaquely colored lines cannot be used.

SUMMARY OF THE INVENTION

It is therefore an object of the invention to provide an intravenous line identification system which has highly visible line source to line output identifiers.

It is another object of the invention to provide an intravenous line identification system which is usable with standard intravenous lines.

It is a further object of the invention to provide an intravenous line identification system which can be quickly applied to intravenous lines.

It is an additional object of the invention to provide an intravenous line identification system which is not prone to misidentification.

It is also an object of the invention to provide an intravenous line identification system which is inexpensive.

It is yet another object of the invention to provide an intravenous line identification system which is reusable.

In accord with these objects which will be discussed in detail below, an intravenous line identification system is provided which includes a plurality of tag sets, each tag set having at least two identifying tags. Each tag set is provided with a highly visible color distinct from the color of every other tag set. A tag in each tag set is coupled to another tag in the set by at least one frangible or decouplable connection.

In general, each tag has an opening (e.g., a slot), enabling the tag to be inserted over the intravenous line, and a preferably circular hole, about which the tag holds the intravenous line. The tags are applied over the intravenous line as a tag set, i.e., while coupled. Once the tag set is on the intravenous line, the tags are separated and slid along the line to identify the source and output of the line with tags having the same color. The process is repeated with distinctly colored tag sets for each intravenous line.

In a preferred embodiment, a plurality of differently color-coded tag sets are provided, each tag set having two identically neon colored plastic wheel-shaped tags. The tags in each set are coupled by three frangible connections, and each tag has a keyhole opening extending from the circumference of the tag toward the axis of the tag. The keyhole opening incorporates a radial slot which receives an intravenous line, and a central round hole preferably through the axis of the tag and through which the intravenous line may extend. The circumferential surface of each tag is preferably provided with a knurled region. In use, a set of tags are placed over an intravenous line and then rotated relative to each other by a health care worker to break the frangible connections, with the knurled region providing an engagement means for the fingers of a health care worker. The separated tags are then moved along the intravenous line away from each other such that one color-coded tag rests about the intravenous line at the medicinal source and the corresponding other tag rests about the line adjacent the medicinal output. Another differently colored set is similarly applied to a second-intravenous line to distinguish the second line from the first.

A number of benefits are provided by the invention. First, due to the high visibility of the tags, quick identification by a health care worker of a medicinal source with its output is possible. It will be appreciated that the preferred colors for the tags (i.e., neon and fluorescent colors) are colors not typically found in a hospital environment, and therefore distinctly identify the tags as intravenous line identifiers. Second, because the tags are provided to the intravenous line while coupled together, any risk of misidentification of a source to an output is eliminated. Third, setup of the identifying tags on an intravenous line is rapid, as the tags may be quickly placed over the line and separated. Fourth, the tags can be manufactured very inexpensively and may be used with currently existing intravenous lines. As a result, overall costs are reduced.

According to a second embodiment of the invention, three tags are provided in each set, thereby providing quick visualization-of the source end, the output end, and a central portion of an intravenous line. According to a third embodiment of the invention, two spherical-shaped tags are coupled together by frangible connections. The tags are preferably made of a foam material. According to a fourth embodiment, two generally tubular-shaped tags, each having a slot along their length, are coupled by a frangible connection. According to a fifth embodiment of the invention, the tags in each set are coupled by decouplable and recouplable connectors. A tag may be rejoined to its mate and re-used. According to a sixth embodiment of the invention, each tag is provided in two portions which are coupled by a preferably live hinge. The portions are closable over and lockable around an intravenous line. The portions may also be unlocked to remove the tags from the line.

According to another preferred aspect of the invention, a series of adhesive-backed labels are provided for use in conjunction with the tags sets. Each label has a colored portion matching one of the colors used for the tag sets, and a neutrally-colored portion upon which notes may be written. In practice, a label having a colored portion corresponding to the color of a tag set placed on intravenous line can be adhered to the chart of a patient, to the medicinal source (i.e., directly to the source bag), or to any other surface in which the label assists the caregiver in identifying medicine being fed to the patient and in treating the patient.

Additional objects and advantages of the invention will become apparent to those skilled in the art upon reference to the detailed description taken in conjunction with the provided figures.

BRIEF DESCRIPTION OF THE DRAWINGS

FIG. 11 is a side elevation of a fifth embodiment of an identifying tag set, with the tags coupled to each other;

FIG. 12 is a perspective view of the tag set shown in FIG. 11, with the tags decoupled from each other;

DETAILED DESCRIPTION OF THE PREFERRED EMBODIMENTS

Figure 1:
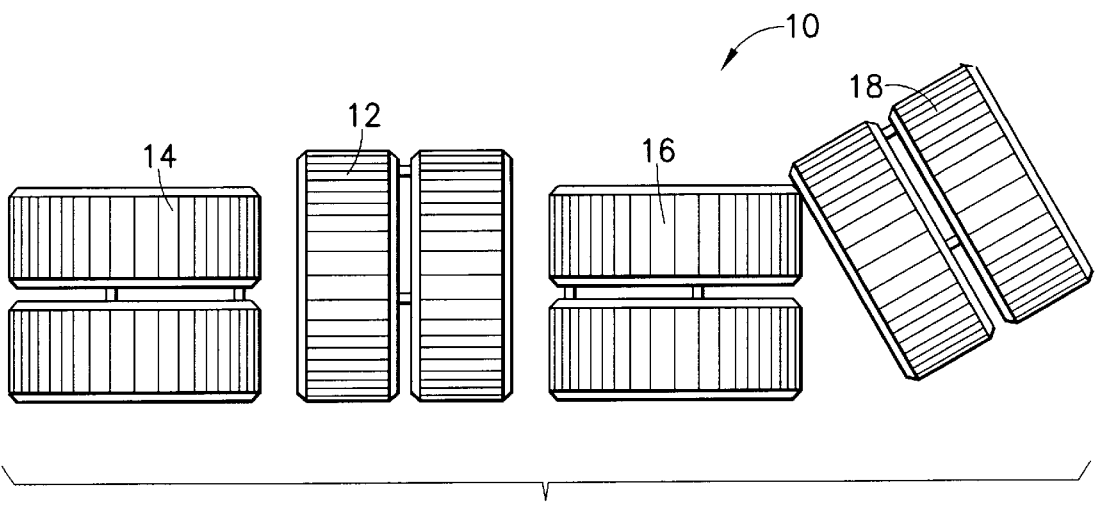
FIG. 1 is a side elevation of an intravenous line identification system having a plurality of tag sets according to the invention.

Turning now to FIG. 1, an intravenous line identification system 10 is shown. The identification system 10 generally includes a plurality of tag sets 12, 14, 16, 18, each including two identifying tags coupled together, as described below. Each of the sets (e.g., set 12) is of a color different than each of the other sets (e.g., sets 14, 16 and 18), and preferably all of the colors are bright high contrast colors, e.g., neon or fluorescent colors. For example, and not by way of any limitation, the identification system may include a bright red tag set 12, a bright yellow tag set 14, a bright green tag set 16, and a bright blue tag set 18, each of the colors of the tag sets being neon in nature.

Figure 2:
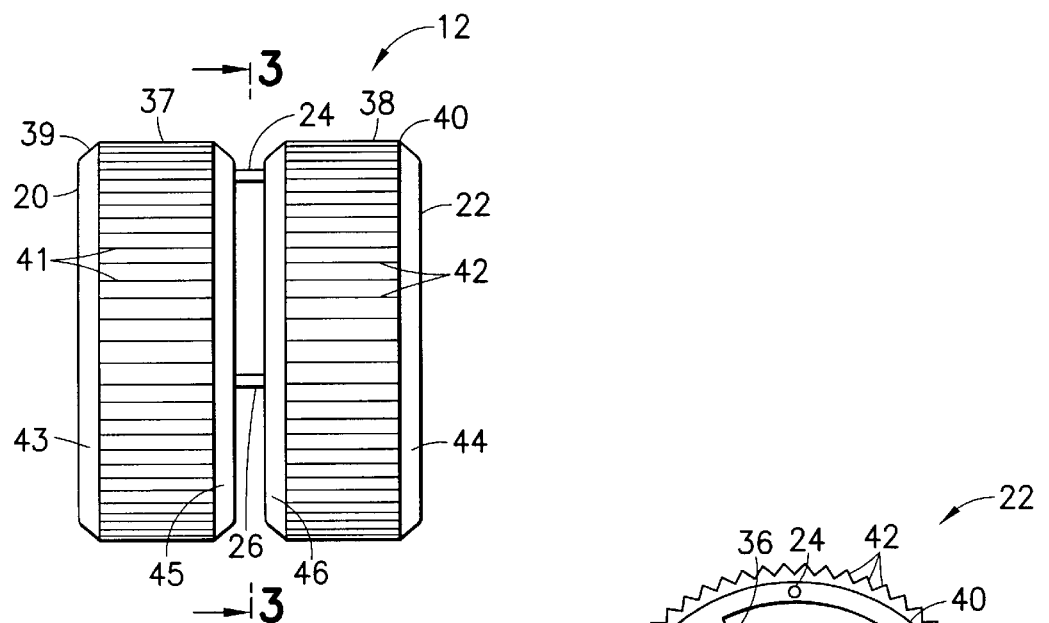
FIG. 2 is a side elevation of a first embodiment of an identifying tag set of the intravenous line identification system shown in FIG. 1.
Figure 3:
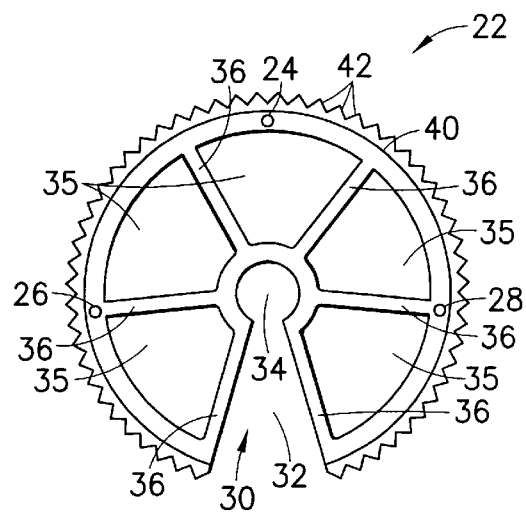
FIG. 3 is a cross-section through line 3–3 in FIG. 2.

Referring now to FIGS. 2 and 3, with respect to tag set 12 (which is preferably the same as the other sets in the system except with respect to color), two identifying tags 20, 22 are coupled by preferably three frangible connections 24, 26, 28. The frangible connections 24, 26, 28 are preferably integrally molded with one of the identifying tags and frictionally locked via an interference fit into holes (not shown) on the other of the identifying tags. Referring to FIG. 3, and described with reference to tag 22 for the purpose of clarity, each tag of the set is preferably wheel-shaped and includes a keyhole opening 30 having a preferably tapered radial slot 32 and a central hole 34 of a diameter substantially the same as the diameter of an intravenous line. Spokes 36 are preferably provided from adjacent the central hole 34 to the peripheral portions of the tag 22 with empty spaces 35 provided therebetween. Referring to FIGS. 2 and 3, a central peripheral portion 37, 38 of the circumferential surface 39, 40 of each tag 20, 22 is preferably provided with knurls 41, 42. The outer peripheral portions 43, 44, 45, 46, surrounding the central peripheral portions 37, 38, are preferably smooth and rounded.

In an illustrative preferred embodiment, the tag set is made from acrylic plastic and each tag has a diameter of approximately one inch and a width of approximately one half inches at the circumferential surface. In addition, the central hole is approximately one-eighth inches in diameter and the radial opening is provided with an approximately 30° angle.

Figure 4:
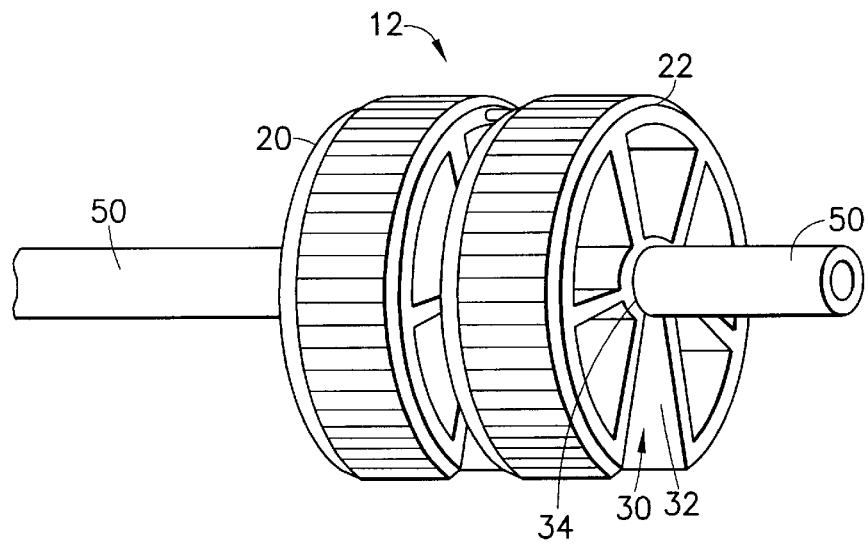
FIG. 4 is a perspective view of the first embodiment of the identifying tag set, with the tag set positioned on an intravenous line.
Figure 5:
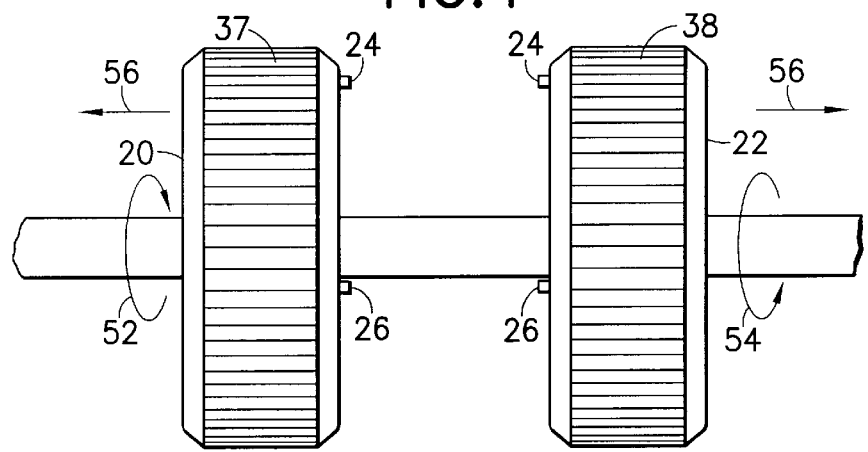
FIG. 5 is a side elevation of the first embodiment of the identifying tag set, with the tags of the tag set positioned on an intravenous line and decoupled from each other.

Turning now to FIG. 4, the tags 20, 22, as a coupled set 12, are pushed together over an intravenous line 50 such that the radial slot 32 of the keyhole opening 30 of each tag extends around the line 50 and the line enters the central hole 34 of each tag. It will be appreciated that the central hole 34 of each tag is sized such that the tag will not substantially constrict the intravenous line 50 and restrict the flow of fluid through the line. Referring to FIGS. 3 and 5, once the tags 20, 22 are located about the line 50, the tags are rotated relative to each other (as indicated by counter-rotational arrows 52, 54) by a health care worker to break the frangible connections 24, 26, 28. The knurled region 37, 38 on each tag provides an engagement means for the fingers of a health care worker to assist in the relative rotation of the tags. Preferably the knurls are sufficiently blunt so as to prevent potential rupture of a latex surgical glove typically worn by health care workers. Once the frangible connections are broken, the tags 20, 22 are moved away from each other (as shown by arrow 56) along the intravenous line 50, such that one tag rests on the intravenous line adjacent the medicinal source and the other tag rests on the line adjacent the medicinal output. For each intravenous line, the process is repeated with other differently colored sets of tags.

The location of the highly visible and differently colored tags along the intravenous lines adjacent the medicinal sources and the outputs permit a health care worker to make a quick identification of one source with its output. It will be appreciated that the preferred colors for the tags (i.e., neon and fluorescent colors) are colors not typically found in a hospital environment, and therefore distinctly identify the tags as intravenous line identifiers. In addition, because the tags are provided to the intravenous line while coupled together, any risk of misidentification of a source to an output is eliminated; i.e., there is practically zero potential for error. Furthermore, setup of the identifying tags on an intravenous line is rapid, as the tags may be rapidly placed over the line and separated, a process requiring minimal labor costs. Moreover, the tags can be manufactured very inexpensively and may be used with currently existing intravenous lines.

Figure 6:
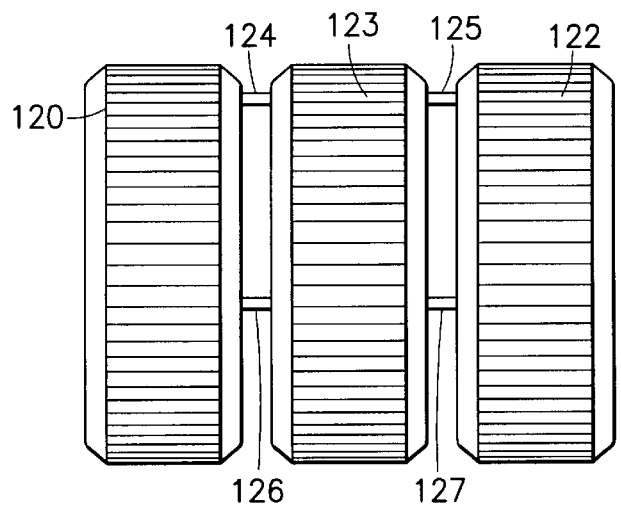
FIG. 6 is a side elevation of a second embodiment of an identifying tag set.

Turning now to FIG. 6, a second embodiment of a tag set 112 for an intravenous line identification system, substantially similar to the first embodiment (with like parts having numbers incremented by 100), is shown. The tag set 112 includes three tags, first and second lateral tags 120, 122 and one central tag 123. The first lateral tag 120 is coupled to the central tag 123 by three frangible connections (shown with respect to two frangible connections 124, 126), and the second lateral tag 122 is coupled to the central tag 123 also by three frangible connections (shown with respect to two frangible connections 125, 127). Each individual tag 120, 122, 123 is substantially the same as described with respect to the first embodiment. When the tags are positioned on an intravenous line and separated from each other, the medicinal source end and output end of the line are indicated (by the first and second lateral tags 120, 122, respectively), as is a central portion of the intravenous line (by the central tag 123).

Figure 7:
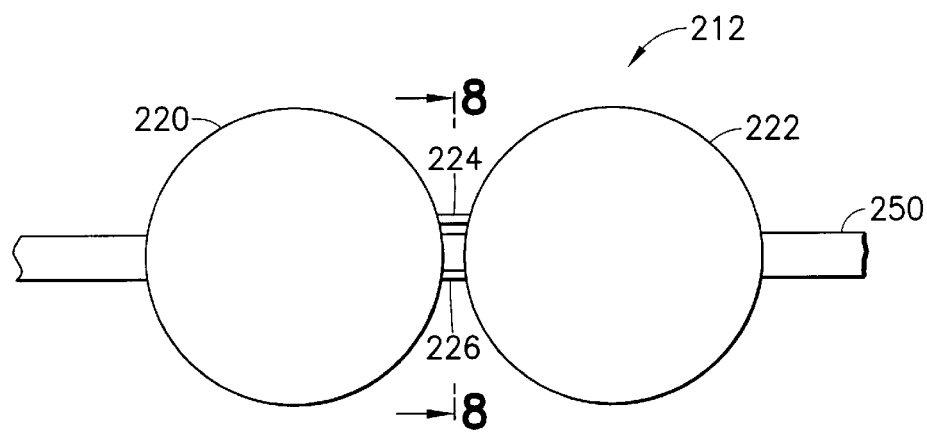
FIG. 7 is a side elevation of a third embodiment of an identifying tag set.
Figure 8:
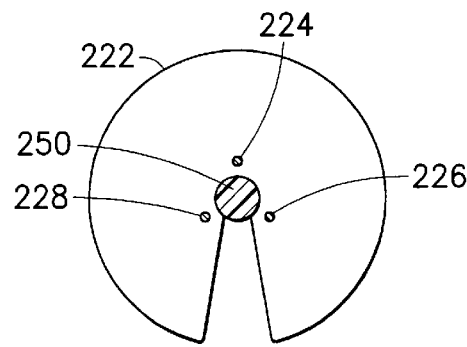
FIG. 8 is a cross section through line 8—8 in FIG. 7.

Referring now to FIGS. 7 and 8, a third embodiment of a tag set 212 for an intravenous line identification system is shown. Each tag 220, 222 in the tag set 212 is substantially spherically shaped. The tags 220, 222 are preferably made from a foam material, e.g., a polyurethane foam, and are coupled together by connectors 224, 226, 228 which are preferably molded integral with tags. The tags 220, 222 are placed over an intravenous line 250 in the same manner as described with respect to the first embodiment and are separated by moving the tags in opposite directions; i.e., pulling the tags apart to either break the connectors or to disconnect the connectors from one or both the tags.

Figure 9:
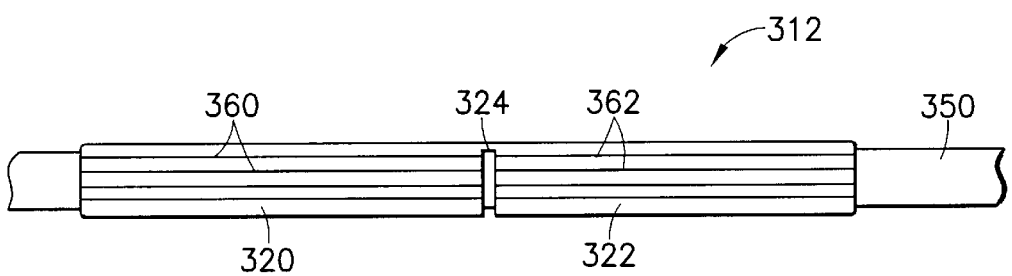
FIG. 9 is a side elevation of a fourth embodiment of an identifying tag set.
Figure 10:
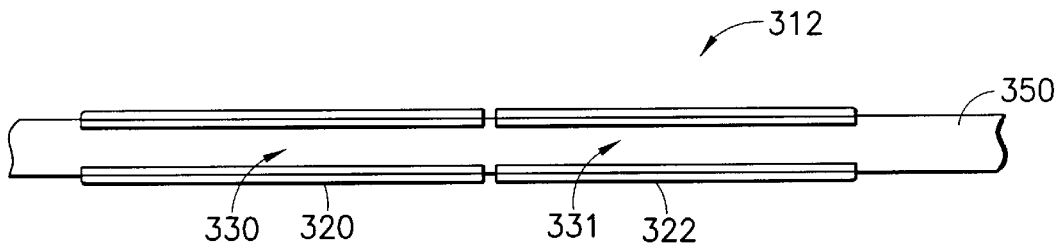
FIG. 10 is a bottom view of the identifying tag set of FIG. 9.

Turning now to FIGS. 9 and 10, a fourth embodiment of a tag set 312 for an intravenous line identification system is shown. The tag set 312 includes two tags 320, 322, each tag 320, 322 being generally tubular in shape. Each tag has a longitudinal opening 330, 331 permitting the tag to be applied onto an intravenous line 350. The tags 320, 322 are coupled by a relatively narrow, frangible bridge 324. Knurls 360, 362 are preferably provided along the length of the tags to assist in separating the tags. The tags may be made from plastic, foam, or any stiff or flexible generally tubular material.

Referring now to FIGS. 11 and 12, a fifth embodiment of a tag set 412 for an intravenous line identification system is shown. The tag set 412 includes two tags 420, 422 (substantially similar to tags 20, 22 described with respect to the first embodiment) which are couplable (FIG. 11), decouplable (FIG. 12), and recouplable (FIG. 11). With reference to FIG. 11, one tag 420 is provided with two slots 462, 464 in the walls 466, 468 bounding the keyhole opening 430 in the tag, and an upper bore 460. The other tag 422 is provided with two tabs 472, 474 extending from the walls 476, 478 bounding the keyhole opening 431 in the tag, and an upper protuberance 470. Each tab 472, 474 is provided with an engagement barb 480, 482.

Figure 13:
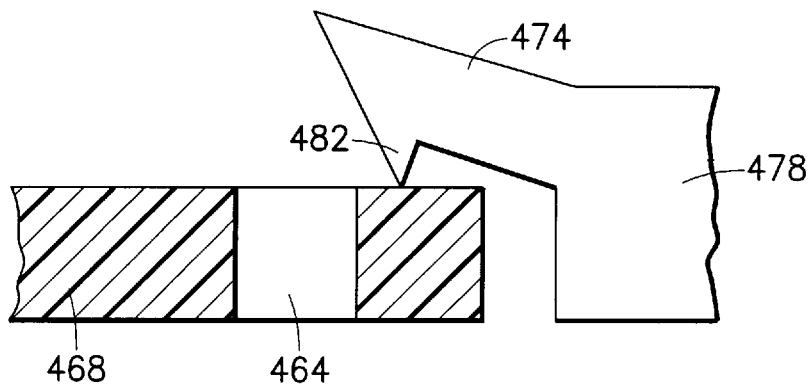
FIGS. 13–15 are enlarged broken top views of the tag set shown in FIG. 11, illustrating the coupling and decoupling mechanism of the tags.
Figure 14:
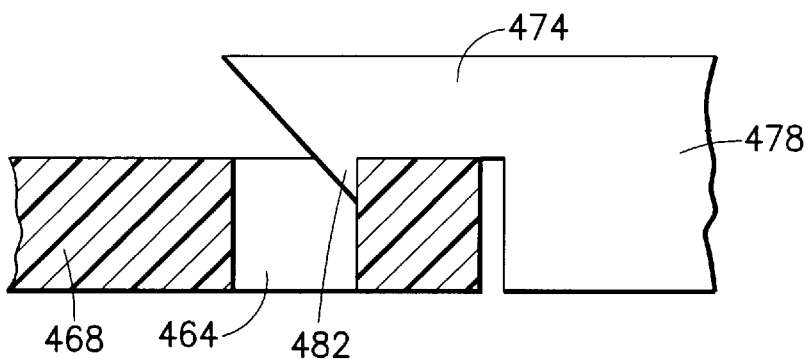
Figure 15:
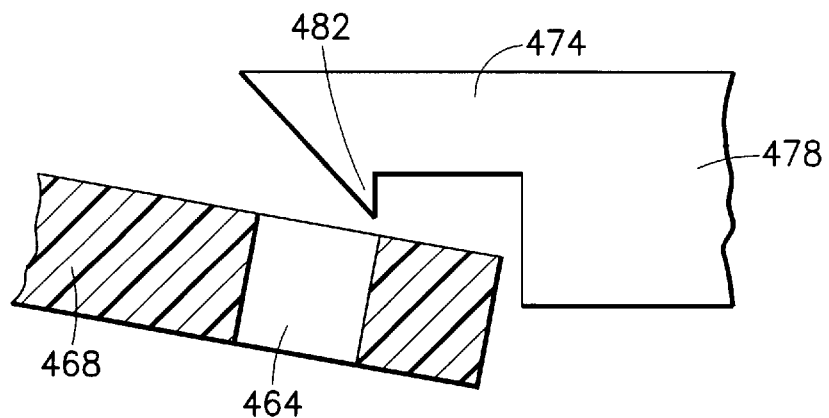

The tags can be coupled together by first aligning the upper protuberance 470 of tag 422 with the upper bore 460 of tag 420. The tags are then pushed together such that the barbs 480, 482 of tag 422 ride over respective walls 466, 468 of tag 420 (shown with respect to one barb 482 in FIG. 13) and seat in slots 462, 464 (FIG. 14). Once seated, the barbs 480, 482 prevent the tags from decoupling and permit the tags to be applied to an intravenous line together as a set. After the tags have been applied to the line, the tags may be decoupled by squeezing tag 420 to move wall 466 relatively toward wall 468. Relative movement of walls 466 and 468 releases the barbs 480, 482 from the slots 462, 464 (shown with respect to one barb 482 and one slot 464 in FIG. 15) and permits the tags 420, 422 to then be moved relatively away from one another. When the tags 420, 422 are no longer needed on a particular intravenous line, the tags may be removed from the line and reassembled as a set for later use.

Figure 16:
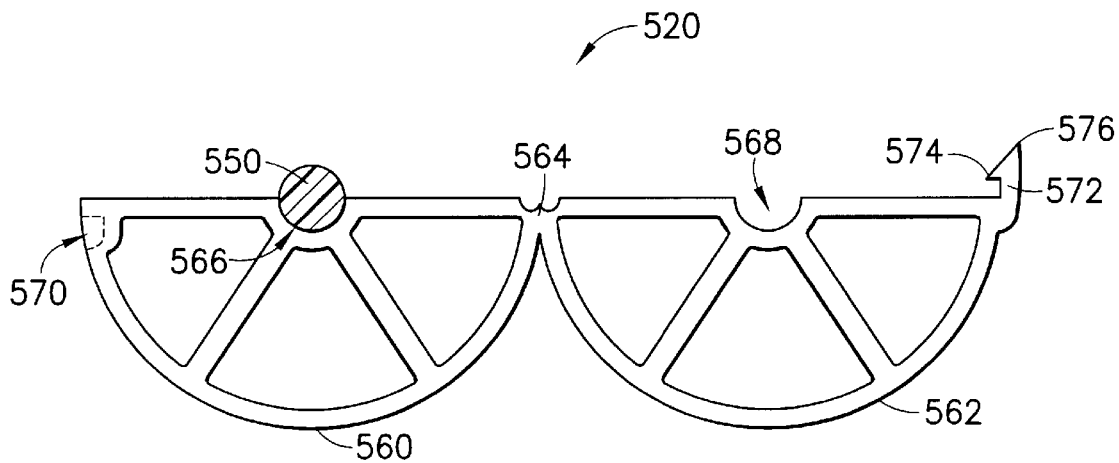
FIG. 16 is a side elevation view a sixth embodiment of an identifying tag set, with one tag of the tag set shown in an open position.
Figure 17:
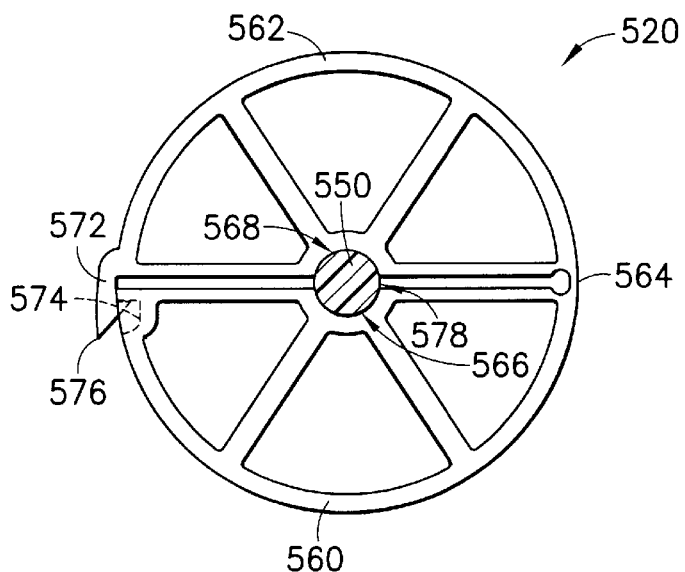
FIG. 17 is a view similar to FIG. 16, with the tag in a closed position.

A sixth embodiment of a tag set for an intravenous line identification system includes at least one tag set having at least two tags, in which the tags are coupled together by any of the means described above. Turning to FIGS. 16 and 17, the tag set is shown with respect to one tag 520. The tag 520 includes two preferably substantially semicircular-shaped portions 560, 562 coupled together by a preferably live hinge 564. Each semicircular portion 560, 562 includes a preferably semicircular cutout 566, 568. In addition, one semicircular-shaped portion 560 includes a locking hole 570 at an end generally opposite the live hinge 564, while the other semicircular-shaped portion includes a tab 572 having a barb 574.

In practice, an intravenous line 550 is placed in one cutout 566 and the two semicircular-shaped portions 560, 562 are rotated toward each other about the hinge 564. The intravenous line 550 is thereby positioned within a hole 578 formed by the two now opposing cutouts 566, 568 (FIG. 17). The locking hole 570 and barb 574 are positioned and sized such that when the semicircular-shaped portions 560, 562 close around the intravenous line, the barb will seat in the locking hole and maintain the tag in a closed position. The individual tags of the tag set may then be separated from each other; e.g., by breaking frangible connections (not shown) between the tags, and moved into their desired position around the intravenous line. It will be appreciated that the barb 574 may be released from the locking hole 570 by moving a release 576 located on the tab 572 in a direction generally opposite the locking hole 570, and thereby opening the tag 520 such that the tag can be removed from the intravenous line.

Figure 18:
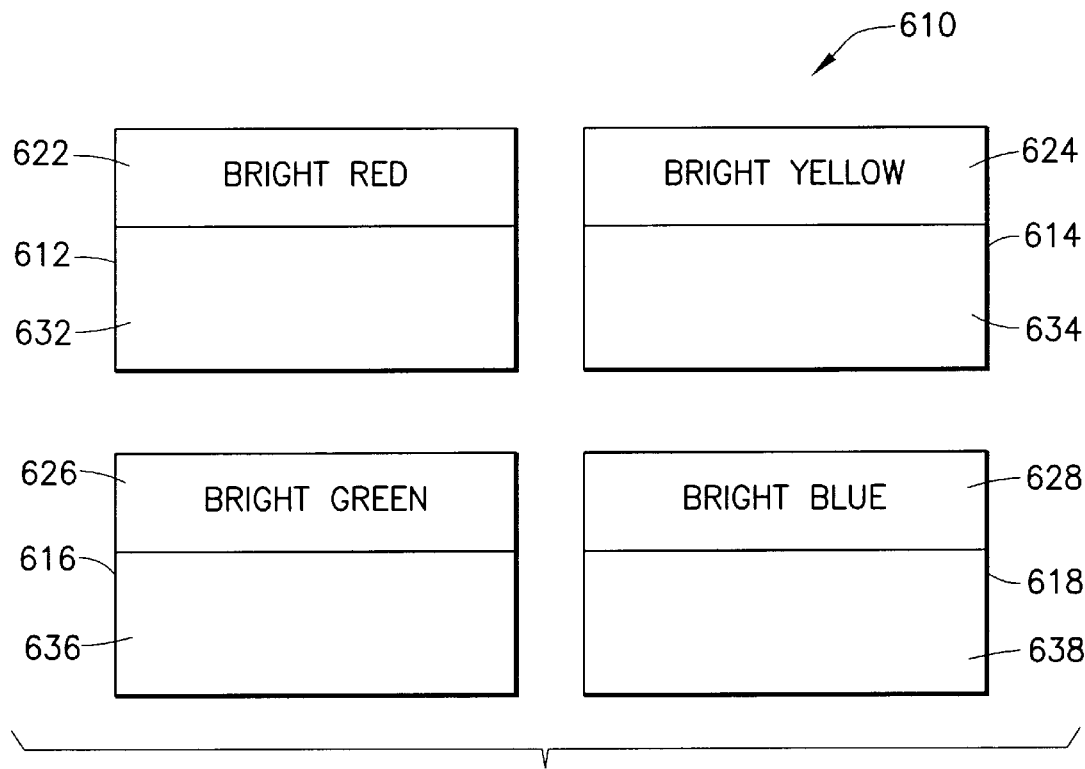
FIG. 18 is a side elevation of a series of labels for use in conjunction with the intravenous line identification system according to the invention.

Turning to FIG. 18 and according to another preferred aspect of the invention, a series 610 of adhesive-backed labels 612, 614, 616, 618 are provided for use in conjunction with the tags sets. Each label has a colored portion 622, 624, 626, 628 matching one of the colors used for the tag sets, and a neutrally-colored portion 632, 634, 636, 638 (e.g., a white portion) upon which notes may be written. The neutrally-colored portion of the label may be provided with medicinal names, caregiver notes (e.g., the time an I.V. drip bag was replaced), and other useful markings.

Figure 19:
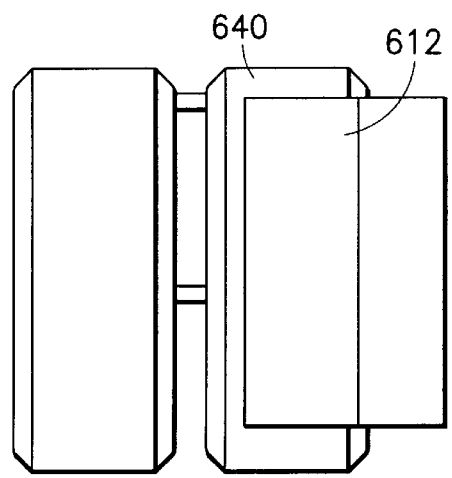
FIG. 19 is a side elevation of an identifying tag set provided with a label according to the invention.

In practice, a label having a colored portion corresponding to the color of a tag set applied to an intravenous line can be adhered to the chart of a patient, to the medicinal source (i.e., directly to the source bag), or to any other surface in which the label assists the caregiver in identifying medicine being fed to the patient and in treating the patient. As shown in FIG. 19, for system integrity, a label 612 may be removably adhered to a tag set 640 for ease of use in conjunction with that tag set. It will also be appreciated that the labels may be provided separately from the tag sets; i.e., on rolls or on sheets.

There have been described and illustrated herein an intravenous line identification system and several embodiments of tag sets therefor. While particular embodiments of the invention have been described, it is not intended that the invention be limited thereto, as it is intended that the invention be as broad in scope as the art will allow and that the specification be read likewise. Thus, while particular shapes for the tags have been disclosed, e.g., tubular, wheel-shaped, and spherical, it will be appreciated that other shapes, preferably easily visible from any angle of view, e.g., cubic and pyramid-shaped, can be used as well. Furthermore, while tag sets having two and three tags have been disclosed, it will be understood that any number of tags greater than two can be used. In addition, while wheel-shaped tags are shown and described as having spokes, it will be understood that the spokes are not required, and that the tag may be substantially solid. Furthermore, while certain configurations have been disclosed with reference to frangible connections or bridges coupling the tags, it will be appreciated that other numbers of connections, types of connections, and placement of connections may be used as well. For example, while certain of the frangible connections have been described as preferably being integrally molded with one of the identifying tags and frictionally locked into holes on the other of the identifying tags, the frangible connections may also be integrally molded to each of the two identifying tags, or may be provided as distinct pieces, the ends of which are each coupled to the tags. In addition, a breakable membrane, an adhesive, tape between the tags, or any means which will hold the tags together as a tag set until the tag set has been applied to an intravenous line and which then may be "broken" relatively easily and quickly by a health care worker may be used. Moreover, while a particular coupling, decoupling, and recouplable mechanism has been described, it will be appreciated that other such mechanisms may be used in a similar manner. For example, and not by limitation, one or more protuberances on one tag may be frictionally engageable in and removable from bores in an adjacent tag. Also, while plastic and polyurethane foam have been disclosed as the manufacturing materials for the tags, it will be appreciated that other materials, e.g., polystyrene, can likewise be used. In addition, while the tags are preferably provided with highly visible colors to quickly and accurately match one tag of a set to another tag of the same set, other high visibility matching indicia, e.g., a system of tag sets may be provided in which the tag sets each have different shapes, stripes of varying width, large type alphanumeric or symbolic indicia, or multiple alphanumeric or symbolic indicia. Furthermore, while the intravenous line identification system has been shown with four tag sets, it will be appreciated that a fewer or greater number of tag sets may be provided in the system. Moreover, while the tags have been shown for use on intravenous lines, it will be appreciated that the tags may also be used on lines between patients and medical devices, e.g., EKG lines, and also on electrical lines between electrical devices and outlets. It will therefore be appreciated by those skilled in the art that yet other modifications could be made to the provided invention without deviating from its spirit and scope as so claimed.

What is claimed is:

1. An intravenous line identification system, comprising:
   a) a hollow intravenous line defining first and second regions; and
   b) a line identifying means having,
      (i) a first portion provided with a first engagement means for engaging said intravenous line and having a first identification means,
      (ii) a second portion provided with a second engagement means for engaging said intravenous line and having a second identification means substantially the same as the first identification means, and
      (iii) coupling means for releasably coupling said first portion to said second portion, said coupling means uncouplable by manual force without the aid of a breaking or cutting implement, said identification system being engaged on said intravenous line with said first portion coupled to said second portion,
      wherein when said first portion is uncoupled from said second portion, at least one of said first and second portions is slidable along said intravenous line relative to the other of said first and second portions such that said first and second portions distinctly identify said first and second regions, respectively, of said intravenous line.

2. An intravenous line identification system according to claim 1, wherein:
   said coupling means is at least one frangible connection.

3. An intravenous line identification system according to claim 1, wherein:
   each of said first and second engagement means for engaging the intravenous line is a keyhole-shaped opening.

4. An intravenous line identification system according to claim 1, wherein:
   said first identification means is a first color provided to said first portion, and said second identification means is said first color provided to said second portion.

5. An intravenous line identification system according to claim 1, further comprising:
   c) a third portion provided with a third engagement means for engaging the intravenous line and a third identification means; and
   d) coupling means for releasably coupling said third portion to said second portion,
      wherein said third identification means distinctly identifies said third portion as a match for said first and second portions.

6. An intravenous line identification system, comprising:
   a) a plurality of hollow intravenous lines; and
   b) a plurality of line identifiers, each of said line identifiers having
      i) a first portion provided with a first engagement means for engaging one of said plurality of intravenous lines and a first identification means,
      ii) a second portion provided with a second engagement means for engaging said one of said plurality of intravenous lines and a second identification means substantially the same as said first identification means, and
      iii) coupling means for coupling said first portion to said second portion, said coupling means uncouplable by manual force without the aid of a breaking or cutting implement,
         wherein each of said line identifiers is engaged on a separate one of said plurality of intravenous lines, with said first portion coupled to said second portion, such that said first and second identification means of each line identifier distinctly identifies one of said plurality of intravenous lines relative to the other of said plurality of intravenous lines.

7. An intravenous line identification system according to claim 6, wherein:
   for each of said plurality of line identifiers, when said first portion is uncoupled from said second portion, at least one of said first and second portions is slidable along the intravenous line relative to the other of said first and second portions such that said first and second portions distinctly identify a first region and a second region, respectively, of the intravenous line.

8. An intravenous line identification system according to claim 6, wherein:
   said coupling means of each of said plurality of line identifiers is at least one frangible connection.

9. An intravenous line identification system according to claim 6, wherein:
   each of said first and second engagement means of each of said plurality of line identifiers is a keyhole-shaped opening.

10. An intravenous line identification system according to claim 6, wherein:
    for each of said plurality of line identifiers, said first identification means is a first color provided to said first portion, and said second identification means is said first color provided to said second portion, wherein said first color is a distinct color for each of said plurality of line identifiers.

11. An intravenous line identification system according to claim 10, wherein:
    said first color of each of said plurality of line identifiers is one of a neon and a fluorescent color.

12. An intravenous line identification system according to claim 10, wherein:
    said coupling means of each of said plurality of line identifiers is at least one frangible connection, and each of said first and second engagement means of each of said plurality of line identifiers is a keyhole-shaped opening.

13. An intravenous line identification system according to claim 6, wherein:
    said first and second portions of each of said plurality of line identifiers is provided with a gripping means.

14. An intravenous line identification system according to claim 6, wherein:
    said first and second portions of each of said plurality of line identifiers is wheel-shaped and has an axis and a periphery, said engagement means comprises a hole through said axis, and a radial slot extends from said periphery to said hole.

15. An intravenous line identification system according to claim 6, wherein:
    said first and second portions of each of said plurality of line identifiers is one of substantially wheel-shaped, spherical, and tubular.

16. An intravenous line identification system according to claim 6, wherein:
    for each of said plurality of line identifiers, said coupling means is also for recoupling said first portion to said second portion.

17. An intravenous line identification system according to claim 16, wherein:

said coupling means comprises a resilient tab on said first portion, said tab having a barb, and a slot provided in said second portion, wherein said barb is engageable in said slot to couple said first portion to said second portion.

18. An intravenous line identification system according to claim 17, wherein:

at least one of said first portion and said second portion is deformable, such that when said first portion is coupled to said second portion said at least one of said first portion and said second portion may be deformed to release said barb from said slot and decouple said first portion from said second portion.

19. An intravenous line identification system according to claim 6, further comprising:

d) first portion member coupling means; and
e) second portion member coupling means,
wherein said first portion further comprises first and second members coupled by and rotatable about a first hinge means, said first and second members being couplable in a closed position about one of the plurality of intravenous lines by said first portion member coupling means for coupling said first and second members, and
said second portion further comprises first and second members coupled by and rotatable about a second hinge means, said first and second members being couplable in a closed position about the same one of the plurality of intravenous lines by said second portion member coupling means for coupling said first and second members.

20. An intravenous line identification system according to claim 19, wherein:

said first portion member coupling means comprises a first barb extending from said first member of said first portion and a first hole provided in said second member of said first portion, said first barb lockingly engageable in said first hole, and said second portion member coupling means comprises a second barb extending from said first member of said second portion and a second hole provided in said second member of said second portion, said second barb lockingly engageable in said second hole.

21. An intravenous line identification system according to claim 6, wherein:

said first and second portions of each of said line identifiers is made from one of a plastic and a foam.

22. An intravenous line identification system according to claim 6, further comprising:

a plurality of label means, each of said plurality of label means being uniquely identified with one of the plurality of line identifiers for providing a writable surface on which information regarding the contents of the one of the intravenous line engaged by said one of the plurality of line identifiers can be provided.

23. An intravenous line identification system according to claim 22, wherein:

for each of said plurality of line identifiers, said first identification means is a first color provided to said first portion, and said second identification means is said first color provided to said second portion, and each of said plurality of label means has a colored portion having a color distinct from the others of said plurality of label means, wherein said first color is a distinct color for each of said plurality of line identifiers and said colored portion of each of said plurality of label means matches said first color of only one of said plurality of line identifiers.

24. An intravenous line system, comprising:

a) a plurality of hollow intravenous lines;
b) a plurality of line identifiers, each of said line identifiers having
   i) a first portion provided with a first identification means and a first engagement means for engaging one of said plurality of intravenous lines,
   ii) a second portion provided with a second identification means substantially the same as said first identification means and a second engagement means for engaging said one of said plurality of intravenous lines, and
   iii) coupling means for releasably coupling said first portion to said second portion without the aid of a breaking or cutting implement; and
b) a plurality of label means, each of said label means uniquely identified with one of said plurality of line identifiers, for providing a writable surface on which information regarding the contents of said one of said plurality of intravenous lines on which said one of said plurality of line identifiers is coupled can be provided,
wherein each of said line identifiers, with said first portion coupled to said second portion, is engaged on a separate one of said plurality of intravenous lines such that said first and second identification means of each line identifier distinctly identifies one of said plurality of the intravenous lines relative to the other of said plurality of intravenous lines.

\* \* \* \* \*